US010947253B2

(12) United States Patent
Blagg et al.

(10) Patent No.: US 10,947,253 B2
(45) Date of Patent: Mar. 16, 2021

(54) FUSED POLYCYCLIC DIMERS

(71) Applicant: Ankh Life Sciences Limited, Dublin (IE)

(72) Inventors: Brian Scott Johnathan Blagg, Niles, MI (US); Vishal Chandrakumar Birar, Mishawaka, IN (US); Gene H. Zaid, Hutchinson, KS (US)

(73) Assignee: Ankh Life Sciences Limited, Dublin (IE)

(*) Notice: Subject to any disclaimer, the term of this patent is extended or adjusted under 35 U.S.C. 154(b) by 59 days.

(21) Appl. No.: 16/531,601

(22) Filed: Aug. 5, 2019

(65) Prior Publication Data
US 2021/0040121 A1    Feb. 11, 2021

(51) Int. Cl.
| C07D 519/00 | (2006.01) |
| C07D 215/06 | (2006.01) |
| C07D 215/14 | (2006.01) |
| C07D 215/20 | (2006.01) |
| C07D 217/20 | (2006.01) |

(52) U.S. Cl.
CPC ......... C07D 519/00 (2013.01); C07D 215/06 (2013.01); C07D 215/14 (2013.01); C07D 215/20 (2013.01); C07D 217/20 (2013.01)

(58) Field of Classification Search
CPC .. C07D 519/00; C07D 215/06; C07D 215/14; C07D 215/20; C07D 217/20
See application file for complete search history.

(56) References Cited

U.S. PATENT DOCUMENTS

| 4,808,718 A | 2/1989 | Harman et al. |
| 4,933,345 A | 6/1990 | Huth et al. |
| 5,095,020 A | 3/1992 | Hulkenberg et al. |
| 5,300,645 A | 4/1994 | Audia et al. |
| 5,332,746 A | 7/1994 | Hamminga et al. |
| 5,350,750 A | 9/1994 | Huth et al. |
| 5,604,236 A | 2/1997 | Jakubowski et al. |
| 6,114,350 A | 9/2000 | Randall et al. |
| 6,350,757 B1 | 2/2002 | Goldstein et al. |
| 6,462,047 B1 | 10/2002 | Bombrun et al. |
| 6,720,331 B2 | 4/2004 | Yeh et al. |
| 7,425,650 B1 | 9/2008 | Chuang |
| 7,550,479 B2 | 6/2009 | Orme et al. |
| 7,615,638 B2 | 11/2009 | Horne et al. |
| 7,732,437 B2 | 6/2010 | Tegtmeier et al. |
| 7,955,718 B2 | 6/2011 | Kambe et al. |
| 8,039,025 B1 | 10/2011 | Zaid et al. |
| 8,450,307 B2 | 5/2013 | Sargent et al. |
| 8,691,801 B2 | 4/2014 | Guzman et al. |
| 8,748,473 B2 | 6/2014 | McKnight et al. |
| 8,815,840 B2 | 8/2014 | Purandare et al. |
| 9,006,246 B2 | 4/2015 | Ohata et al. |
| 9,034,865 B2 | 5/2015 | Chakravarty et al. |
| 9,162,980 B2 | 10/2015 | McKnight et al. |
| 9,168,247 B2 | 10/2015 | Frederick et al. |
| 9,193,957 B2 | 11/2015 | Chen et al. |
| 9,271,971 B2 | 3/2016 | Jain et al. |
| 9,290,476 B2 | 3/2016 | Leonard et al. |
| 9,402,834 B2 | 8/2016 | Zaid et al. |
| 9,593,115 B2 | 3/2017 | Barawkar et al. |
| 9,725,449 B2 | 8/2017 | Norris et al. |
| 10,011,614 B2 | 7/2018 | Wang et al. |
| 10,072,009 B2 | 9/2018 | Bharate et al. |
| 10,086,000 B2 | 10/2018 | Fischer et al. |
| 10,092,550 B2 | 10/2018 | Zaid et al. |
| 10,125,114 B2 | 11/2018 | Bradner et al. |
| 10,138,242 B2 | 11/2018 | Sattler et al. |
| 2006/0167259 A1 | 7/2006 | Chao et al. |
| 2006/0217410 A1 | 9/2006 | Chen et al. |
| 2008/0069899 A1 | 3/2008 | Jossang born Yanagida et al. |
| 2008/0221221 A1 | 9/2008 | Zhou et al. |
| 2009/0093517 A1 | 4/2009 | Graulich et al. |
| 2009/0227619 A1 | 9/2009 | Wu et al. |
| 2011/0002855 A1 | 1/2011 | Caldwell et al. |
| 2011/0245503 A1 | 10/2011 | Santos et al. |
| 2012/0058208 A1 | 3/2012 | Jacob |
| 2012/0108556 A1 | 5/2012 | Zaid et al. |
| 2013/0116219 A1 | 5/2013 | Ellis et al. |
| 2015/0315188 A1 | 11/2015 | Protter et al. |
| 2016/0039845 A1 | 2/2016 | Wang et al. |
| 2016/0318928 A1 | 11/2016 | Norris et al. |
| 2016/0326166 A1 | 11/2016 | Wang et al. |
| 2017/0042865 A1 | 2/2017 | Zaid et al. |
| 2017/0369507 A1 | 12/2017 | Christian et al. |

(Continued)

FOREIGN PATENT DOCUMENTS

| CN | 106977515 A | 4/2017 |
| CN | 102796124 B | 6/2017 |

(Continued)

OTHER PUBLICATIONS

Hamer, F., 123 J. Chem. Soc., Trans. 246-59 (1923) (CAS Abstract) (Year: 1923).*
Skidmore et al., J. Chem. Soc. 1641-5 (1959) (CAS Abstract) (Year: 1959).*
Misra et al., 39 J. Indian Chem. Soc., 321-4 (1962) (CAS Abstract) (Year: 1962).*
Jin et al., 69(32) Tetrahedron 6579-6584 (2013) (CAS Abstract) (Year: 2013).*
Cannon, J.G, Chapter Nineteen in "Burger's Medicinal Chemistry and Drug Discovery, Fifth Edition, Volume 1: Principles and Practice." *Wiley-Interscience* 1995, pp. 738-802.
Cao et al. "Synthesis and cytotoxic activities of 1-benzylidine substituted ß-carboline derivatives." *Bioorg. Med. Chem. Lett.* 18/24 (2008): 6558-6561.

(Continued)

*Primary Examiner* — Timothy R Rozof
(74) *Attorney, Agent, or Firm* — Hovey Williams LLP

(57) ABSTRACT

Novel fused tricyclic or bicyclic dimers, such as β-carboline and quinoline moieties with a central linker, exhibit anti-cancer activities against a variety of human cancer cell lines. The dimer compounds can be used in anti-cancer therapeutic compositions useful in the treatment of human cancers.

15 Claims, No Drawings

(56) References Cited

U.S. PATENT DOCUMENTS

| | | |
|---|---|---|
| 2018/0022747 A1 | 1/2018 | Meng et al. |
| 2018/0155299 A1 | 6/2018 | Birudukota et al. |
| 2018/0251459 A1 | 9/2018 | Hubin et al. |
| 2018/0291020 A1 | 10/2018 | Haddach |
| 2018/0297999 A1 | 10/2018 | Boloor et al. |
| 2018/0319804 A1 | 11/2018 | Lim et al. |
| 2019/0152970 A1 | 5/2019 | Labadie et al. |

FOREIGN PATENT DOCUMENTS

| | | |
|---|---|---|
| CN | 107880040 A | 12/2017 |
| CN | 108191863 A | 4/2018 |
| EP | 2050747 A1 | 4/2009 |
| EP | 3091015 A1 | 11/2016 |
| FR | 2869540 A1 | 11/2005 |
| GB | 2304712 A | 3/1997 |
| WO | 2008150899 A1 | 12/2008 |
| WO | 2009003147 A1 | 12/2008 |
| WO | 2009047298 A2 | 4/2009 |
| WO | 2011133795 A2 | 10/2011 |
| WO | 2015006646 A1 | 1/2015 |
| WO | 2016064676 A1 | 4/2016 |
| WO | 2016181220 A2 | 11/2016 |
| WO | 2017146220 A1 | 8/2017 |

OTHER PUBLICATIONS

Charlet-Fabnere et al. "Synthesis of Large-Ring Bis-Indolic Dilactams." *Tetrahedron Letters* 40 (1999): 1-4.

Chatwichien et al. "Design, Synthesis and Biological Evaluation of β-Carboline Dimers Based on the Structure of Neokauluamine." *Tetrahedron Lett.* Jun. 3, 2015; 56(23): 3515-3517.

Dalpozzo. "Strategies for the asymmetric functionalization of indoles: an update." *Chem. Soc. Rev.*, 2015, 44, 742.

Du et al. Synthesis and Antitumor Activity of beta-carboline dimmers. In: The $9^{th}$ Chinese National Conference on Chemical Biology, Aug. 28-31, 2015, pp. 1-222 [online]. Available online at http://or.nsfc.gov.cn/bitstream/00001903-5/401410/1/1000014265298.pdf#page=208>; p. 187, first paragraph; p. 187, figure 1.

Durant et al. "Vanillins-a novel family of DNA-PK inhibitors." *Nucleic Acids Research* 31.19 (2003): 5501-5512.

El-Sharkawy et al. "New Approaches for the Synthesis and Antitumor Evaluation of Pyridine, Thieno[3,4-c]Pyridine, Pyrazolo[3,4-b]Pyridine and Pyrido[3,4-d]Pyridazine Derivatives." *Eur. Chem. Bull.*, 2013, 2(8), 530-537.

Fischer et al., "Über Harmin und Harmalin." *Ber. Deutsch. Chem. Gesel.* 47/1 (1914): 99-107.

Gu et al. "Synthesis and In Vitro Antitumor Activity of Novel Bivalent β-Carboline-3-carboxylic Acid Derivatives with DNA as a Potential Target." *Int. J. Mol. Sci.*, 2018, 19 3179.

Guo et al. (1) "Synthesis and preliminary evaluation of novel alkyl diamine linked bivalent β-carbolines as angiogenesis inhibitors." *MedChemComm*, Nov. 1, 2016, Issue 11, 2017-2183. Abstract only.

Guo et al. (2) "Synthesis and structure-activity relationships of asymmetric dimeric β-carbolines derivatives as potential antitumor agents." *European Journal of Medicinal Chemistry* 147:10 2018, 253-265.

Hakkarainen, K.M. et al. "Prevalence and Perceived Preventability of Self-Reported Adverse Drug Events—A Population-Based Survey of 7,099 Adults." *PLoS One* 8.9 (2013): e73166.

Hsiao, et al. "Mana-Hox displays anticancer activity against prostate cancer cells through tubulin depolymerization and DNA damage stress." *Naunyn-Schmiedeberg's Arch Pharmacol* (2008) 378: 599-608

Husbands et al. "β-carboline binding to imidazoline receptors." *Drug and Alcohol Dependence* 64 (2001) 203-208.

Ikeda et al. "3-Benzylamino-β-carboline derivatives induce apoptosis through G2/M arrest in human carcinoma cells HeLa S-3." European Journal of Medicinal Chemistry, 46 (2011) 636-646.

International Search Report and Written Opinion ($1^{st}$ of 2) dated Sep. 5, 2016, PCT/IB2016/000723, International Filing Date Apr. 20, 2016.

International Search Report and Written Opinion ($2^{nd}$ of 2) dated Nov. 21, 2016, PCT/IB2016/000723, International Filing Date Apr. 20, 2016.

International Search Report and Written Opinion dated Aug. 14, 2017, PCT/IB2017/000529, International Filing Date Apr. 19, 2017.

International Search Report and Written Opinion dated Jan. 29, 2018, PCT/US2017/059299, International Filing Date Oct. 31, 2017.

International Search Report and Written Opinion dated Sep. 14, 2018, PCT/US2018/033018, International Filing Date May 16, 2018.

International Search Report and Written Opinion dated Sep. 18, 2018, PCT/US2018/038533, International Filing Date Jun. 20, 2018.

International Search Report and Written Opinion dated Feb. 12, 2019, PCT/US2018/066814, International Filing Date Dec. 20, 2018.

International Search Report and Written Opinion dated Sep. 3, 2019, PCT/US2019/032510, International Filing Date May 15, 2019.

Jiang et al. "Cytotoxic Bis-3,4-dihydro-β-carbolines and Bis-β-carbolines." *Journal of Enzyme Inhibition and Medicinal Chemistry* 2002 17.6, 369-374.

Kaur et al. "Antimalarials from nature." *Bioorganic & Medicinal Chemistry*, Article in Press. (2009) 28 pages.

Luo et al. "Anti-cancer Effects of JKA97 Are Associated with Its Induction of Cell Apoptosis via a Bax-dependent and p53-independent Pathway." *The Journal of Biological Chemistry* 283. 13, (2008), 8624-8633.

Muller et al. "Exciton Fission and Fusion in Bis(tetracene) Molecules with Different Covalent Linker Structures." *J. Am. Chem. Soc.* 129 (2007) 14240-14250.

Nekkanti et al. "Targeting DNA Minor Groove by Hybrid Molecules as Anticancer Agents." *Current Medicinal Chemistry*, 2017, 24 2887-2907.

Obach, R.S. "Drug-Drug Interactions: An Important Negative Attribute in Drugs." Drugs Today 39.5 (2003): 308-338 (Abstract only).

Office Action dated Nov. 20, 2018, in U.S. Appl. No. 16/013,504, filed Jun. 20, 2018.

Patel, P.S. et al. "A Study of Potential Adverse Drug-Drug Interactions Among Prescribed Drugs in a Medicine Outpatient Department of a Tertiary Care Teaching Hospital." *J. Basic Clin. Pharm.* 5.2 (2014): 44-48.

Peng et al. "Structure—Activity Relationship and Mechanism of Action Studies of Manzamine Analogues for the Control of Neuroinflammation and Cerebral Infections." *J. Med. Chem.* 53 (2010) 61-76.

Perkin et al. "CXC—Harmine and Harmaline, Part 1." *J. Chem. Soc. Trans.* 101 (1912): 1775-87.

Ponra et al. "Bronsted acid-promoted synthesis of common heterocycles and related bio-active and functional molecules." *RSC Adv.* 2016, 6, 37784.

Pouilhes et al. "6',7-Dihydrokeramamine C and analogues: synthesis and biological evaluation." *Tetrahedron* 42/47 (2001): 8297-9.

PUBCHEM-CID 84053302 Create Date: Oct. 20, 2014; pp. 1-10; p. 3, Fig. Found online at https://pubchem.ncbi.nlm.nih.gov/compound/84053302, Aug. 10, 2018.

Rescigno et al. "Vanilloid Derivatives as Tyrosinase Inhibitors Driven by Virtual Screen-Based QSAR Models." *Drug Test Analysis* 3 (2011): 176-191.

Rook et al. "Bivalent β-Carbolines as Potential Multitarget Anti-Alzheimer Agents." *J. Med. Chem.* 2020, 53, 3611-3617.

Samundeeswari et al. "Design and synthesis of novel phenyl-1,4-beta-carboline-hybrid molecules as potential anticancer agents." *European Journal of Medical Chemistry* 128 (2017) 123-139.

Shen et al. "Synthesis of 1-Substituted Carbazolyl-1,2,3,4-tetrahydro- and Carbazolyl-3,4-dihydro-β-Carboline Analogs as Potential Antitumor Agents." *Mar. Drugs* 9, (2011) 256-277.

Song, et al. "β-Carbolines as Specific Inhibitors of Cyclin-Dependent Kinases." *Bioorganic & Medicinal Chemistry Letters* 12 (2002 1129-1132.

(56) References Cited

OTHER PUBLICATIONS

Sotiropoulou et al. "Chemical Approaches to Targeting Drug Resistance in Cancer Stem Cells." *Drug Discovery Today* 19.10 (Oct. 2014): 1547-1562.

Tu et al. "The β-Carboline Analog Mana-Hox Causes Mitotic Aberration by Interacting with DNA." *Chemistry & Biology* 12 (2005): 1317-1324.

Wang, et al. "Synthesis of carbon-aa-labeled bivalent β-carbolines as new PET agents for imaging of cholinesterase in Alzheimer's disease." *Applied Radiation and Isotopes*, 69 (2011) 678-685.

Weiqun et al. "β-Carbolines. 1. Synthesis of Several New Bis-β-carboline Compounds." *Journal of Chinese Pharmaceutical Sciences* 8:3 (1999): 177-179.

Yadev et al. "Telomerase Inhibition and Human Telomeric G-Quadruplex DNA Stabilization by a β-Carboline-Benzimidazole Derivative at Low Concentrations." *Biochemistry* 56 (2017) 4392-4404.

Yin et al. "Synthesis of bivalent ligands of β-Carboline-3-carboxylates via a palladium-catalyzed homocoupling process." Tetrahedron Letters 46 (2005) 6363-6368.

Zhang, Yimao et al. "Identification of Inhibitors of ABCG2 by a Bioluminescence Imaging-Based High-Throughput Assay." *Cancer Res* 69 (2009): 5867-5876.

Zhang, Xiao-Fei et al. "Synthesis and mechanisms of action of novel harmine derivatives as potential antitumor agents." Scientific Reports 6:33204 (2016): 1-16.

Zhu et al. "Indole Alkaloids from *Alocasia macrorrhiza*." *Chem. Pharm. Bull.* 60:5 (2012) 670-673.

International Search Report and Written Opinion dated Jan. 4, 2021, in PCT/US2020/044567, International Filing Date Jul. 31, 2020.

PUBCHEM-CID 46708588 Create Date: Jul. 26, 2010; pp. 1-8. Found online at https://pubchem.ncbi.nlm.nih.gov/compound/46708588, Nov. 30, 2020.

Dai et al. "Beta-Carboline alkaloid monomers and dimers: Occurrence, structrual diversity, and biological activities,"European Journal of Medicinal Chemistry, 2018, vol. 157, pp. 622-656.

Du et al. "Synthesis and biological evaluation of bivalent beta-carbolines as potential anticancer agents," Med. Chem. Commun. 2016, vol. 7, pp. 636-646.

PUBCHEM-CID 132563536 Create Date: Apr. 8, 2018; pp. 1-7. Found online at https://pubchem.ncbi.nlm.nih.gov/compound/132563536, Nov. 30, 2020.

PUBCHEM-CID 102496256 Create Date: Dec. 28, 2015; pp. 1-7. Found online at https://pubchem.ncbi.nlm.nih.gov/compound/102496256, Nov. 30, 2020.

Kitanovic et al. "A Deadly Organometallic Luminescent Probe: Anticancer Activity of a Re' Bisquinoline Complex," Chem. Eur. J. 2014, vol. 20, pp. 2496-2507.

PUBCHEM-CID 72163367 Create Date: Dec. 2, 2013; pp. 1-7. Found online at https://pubchem.ncbi.nlm.nih.gov/compound/72163367, Nov. 30, 2020.

* cited by examiner

FUSED POLYCYCLIC DIMERS

BACKGROUND OF THE INVENTION

Field of the Invention

The present invention is broadly directed to novel fused polycyclic dimers having anti-cancer activities, therapeutic compositions including the compounds, as well as methods of use thereof. More particularly, the invention provides dimers having two fused tricyclic (e.g., β-carbolines such as harmaline) or two fused bicyclic (e.g., quinoline and isoquinoline) moieties with a central linker.

Description of the Prior Art

Cancer is a generic term for a large group of diseases that can affect any part of the body. Other terms used are malignant tumors and neoplasms. One defining feature of cancer is the rapid creation of abnormal cells that grow beyond their usual boundaries, and which can then invade adjoining parts of the body and spread to other organs. This process is referred to as metastasis. Metastases are the major cause of death from cancer.

The transformation from a normal cell into a tumor cell is a multistage process, typically a progression from a precancerous lesion to malignant tumors. These changes are the result of the interaction between a person's genetic factors and three categories of external agents, including:
- physical carcinogens, such as ultraviolet and ionizing radiation
- chemical carcinogens, such as asbestos, components of tobacco smoke, aflatoxin (a food contaminant) and arsenic (a drinking water contaminant)
- biological carcinogens, such as infections from certain viruses, bacteria or parasites.

Some examples of infections associated with certain cancers:
- Viruses: hepatitis B and liver cancer, Human Papilloma Virus (HPV) and cervical cancer, and human immunodeficiency virus (HIV) and Kaposi sarcoma.
- Bacteria: *Helicobacter pylori* and stomach cancer.
- Parasites: schistosomiasis and bladder cancer.

Aging is another fundamental factor for the development of cancer. The incidence of cancer rises dramatically with age, most likely due to a buildup of risks for specific cancers that increase with age. The overall risk accumulation is combined with the tendency for cellular repair mechanisms to be less effective as a person grows older.

Tobacco use, alcohol use, low fruit and vegetable intake, and chronic infections from hepatitis B (HBV), hepatitis C virus (HCV) and some types of Human Papilloma Virus (HPV) are leading risk factors for cancer in low- and middle-income countries. Cervical cancer, which is caused by HPV, is a leading cause of cancer death among women in low-income countries. In high-income countries, tobacco use, alcohol use, and being overweight or obese are major risk factors for cancer.

The most common cancer treatment modalities are surgery, chemotherapy, and radiation treatments. All of these techniques have significant drawbacks in terms of side effects and patient discomfort. For example, chemotherapy may result in significant decreases in white blood cell count (neutropenia), red blood cell count (anemia), and platelet count (thrombocytopenia). This can result in pain, diarrhea, constipation, mouth sores, hair loss, nausea, and vomiting.

Biological therapy (sometimes called immunotherapy, biotherapy, or biological response modifier therapy) is a relatively new addition to the family of cancer treatments. Biological therapies use the body's immune system, either directly or indirectly, to fight cancer or to lessen the side effects that may be caused by some cancer treatments.

During chemotherapies involving multiple-drug treatments, adverse drug events are common, and indeed toxicities related to drug-drug interactions are one of the leading causes of hospitalizations in the US. Obach, R. S. "Drug-Drug Interactions: An Important Negative Attribute in Drugs." *Drugs Today* 39.5 (2003): 308-338. In fact, in any single-month period, one-fifth of all surveyed adults in the USA reported an adverse drug response. Hakkarainen, K. M. et al. "Prevalence and Perceived Preventability of Self-Reported Adverse Drug Events—A Population-Based Survey of 7,099 Adults." *PLoS One* 8.9 (2013): e73166. A large-scale study of adults aged 57-85 found that 29% were taking more than five prescription medications and nearly 5% were at risk of major adverse drug-drug interactions. In the field of oncology, a review of over 400 cancer patients determined that 77% were taking drugs that were considered to have a moderately severe potential for adverse drug interactions, and 9% had major adverse drug interactions. Ghalib, M. S. et al. "Alterations of Chemotherapeutic Pharmocokinetic Profiles by Drug-Drug Interactions." *Expert Opin. Drug Metabl. Toxicol* 5.2 (2009): 109-130.

Such interactions are a global health problem, and the WHO has determined that negative drug interactions are leading causes of morbidity and mortality around the world, with up to 7% of all hospitalizations in the US due to negative drug interactions. A recent survey of a single hospital shows that 83% of hospitalized patients were prescribed drug combinations with the potential to cause adverse reactions. Patel, P. S. et al. "A Study of Potential Adverse Drug-Drug Interactions Among Prescribed Drugs in a Medicine Outpatient Department of a Tertiary Care Teaching Hospital." *J. Basic Clin. Pharm.* 5.2 (2014): 44-48.

Examples of famous negative drug interactions include the development of rhabdomyolysis, a severe muscle disease, when taking Simvastatin with Amiodarone. As a result, the FDA introduced a warning on the drug label about the interaction. The calcium channel blocker Mibefradif, taken for high blood pressure, was removed from the market because of the harmful interaction with drugs that work on the electrical activity of the heart.

U.S. Pat. No. 8,039,025 describes cancer treatments in the form of extracts of *Arum palaestinum* Boiss, supplemented with individual amounts of β-sitosterol, isovanillin, and linoleic acid, and this patent is incorporated by reference herein in its entirety.

U.S. Pat. No. 9,402,834, issued Aug. 2, 2016, describes anti-cancer compositions containing various components in mixtures, such as curcumin, harmine, and isovanillin component mixtures, or component mixtures containing curcumin/harmine, curcumin/isovanillin, and harmine/isovanillin components.

US Patent Publication No. 2016/0039845 to Wang et al. describes dimers comprising two β-carboline moieties with a central (CH2)n alkyl linker, where n ranges from 4-10.

Despite the immense amount of worldwide research and efforts to stem the tide of cancer and its side effects, the disease in its many manifestations continues to be a huge problem. Therefore, any new cancer treatment having a curative affect and/or the ability to ameliorate cancer symptoms and improve the lifestyle of patients is highly significant and important.

SUMMARY OF THE INVENTION

The present invention provides compositions which may be used as improved chemotherapeutics for treatment of humans, and especially in the treatment of human cancers, and corresponding methods for preparing such compositions and use thereof. Generally speaking, the chemotherapeutics of the invention comprise (or consist essentially of, or consist of) one or more compounds or agents, and/or the derivatives (e.g., analogs), isomers, enantiomers, tautomers, esters, complexes, and salts thereof. As used herein, "isomers" refers to each of two or more compounds with the same formula but with at different arrangement of atoms, and includes structural isomers and stereoisomers (e.g., geometric isomers and enantiomers); "tautomers" refers to two or more isometric compounds that exist in equilibrium, such as keto-enol and imine and enamine tautomers. The compounds or agents can be directly used in partial or essentially completely purified forms, or can be modified to provide therapeutically effective, pharmaceutically acceptable, reduced products (produced, e.g., by hydrogenation of the original compounds or agents), as well as esters, metal complexes (e.g., Cu, Fe, Zn, Pt, V), and salts of the foregoing; the compounds may be in crystalline or amorphous forms, and may be lypholized.

The invention also provides new methods for treatment of cancers by administration of appropriate quantities of the compounds hereof Hence, the compositions are particularly designed for use in the treatment of cancers, and the compositions can be used for the manufacture of medicaments for anti-cancer therapeutic applications. In addition, the invention provides compositions for the treatment of cancers comprising administering therapeutically effective amounts of the new compositions, prepared by processes known per se, with a pharmaceutically acceptable carrier.

A "chemotherapeutic," "chemotherapeutic agent," or simply "therapeutic agent," as used herein refers to one or more of the compounds described herein as useful in the treatment of human conditions, especially human cancers. Chemotherapeutics may be cytostatic, selectively toxic or destructive of cancerous tissue and/or cells, including cancer stem cells, but also include indiscriminately cytotoxic compounds used in cancer treatments.

The therapeutic compounds or agents of the invention have been found to be effective in the treatment of a number of human cancer cells, and especially pancreatic, endometrial, breast, lung, ovarian, renal, cervical, lymphoma, and myeloma.

The novel compounds of the invention exhibit anti-cancer activity against a variety of cancer cell lines. One class of these compounds comprises two fused tricyclic moieties with a linker, and has the structure

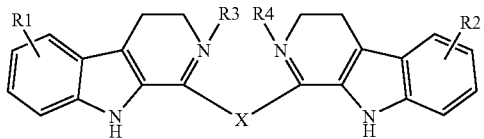

where R1 and R2 are independently selected from the group consisting of H, C1-C4 alkyl groups, and C1-C4 alkoxy groups, R3 and R4 are independently selected from the group consisting of nothing, H, and C1-C2 alkyl groups, and X is selected from the group consisting of (CH2)3 and C3-C8 geminal alkyl groups having a carbon atom therein with two functional groups bound to the carbon atom; the functional groups are independently selected from the group consisting of C1-C3 alkyl groups, C1-C3 alcohols, and metal atoms. In certain embodiments, R1 and R2 are each methoxy groups, R3 and R4 are nothing, and X is either the propyl moiety (CH2)3 or a C3 geminal alkyl groups, where the functional groups are both methyl groups. As used herein, where any R substituent bond line extends into an indeterminant position of a ring, the R substituent can be bound to any possible ring position.

Representative compounds of this class include

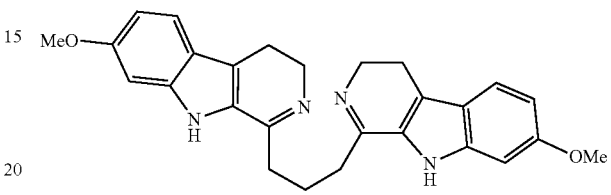

and

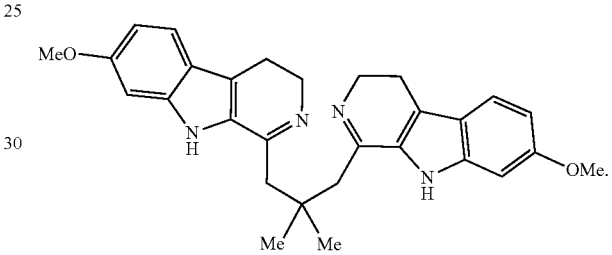

Another class of novel compounds comprises two fused bicyclic moieties with an alkyl phenyl linker according to the following structures

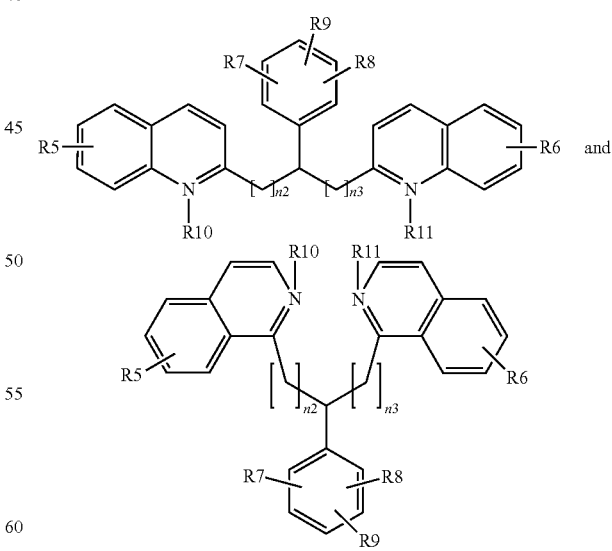

where R5 and R6 are independently selected from the group consisting of H, C1-C4 alkyl groups, and C1-C4 alkoxy groups, R7, R8, and R9 are independently selected from the group consisting of H, OH, C1-C4 alkoxy groups, C1-C4 alkyl groups, —N2, and CH2N2, and n2 and n3 are independently 1-4, and R10 and R11 are independently selected from the group consisting of nothing, H, and C1-C2 alkyl groups.

Certain representative compounds in accordance with this class include

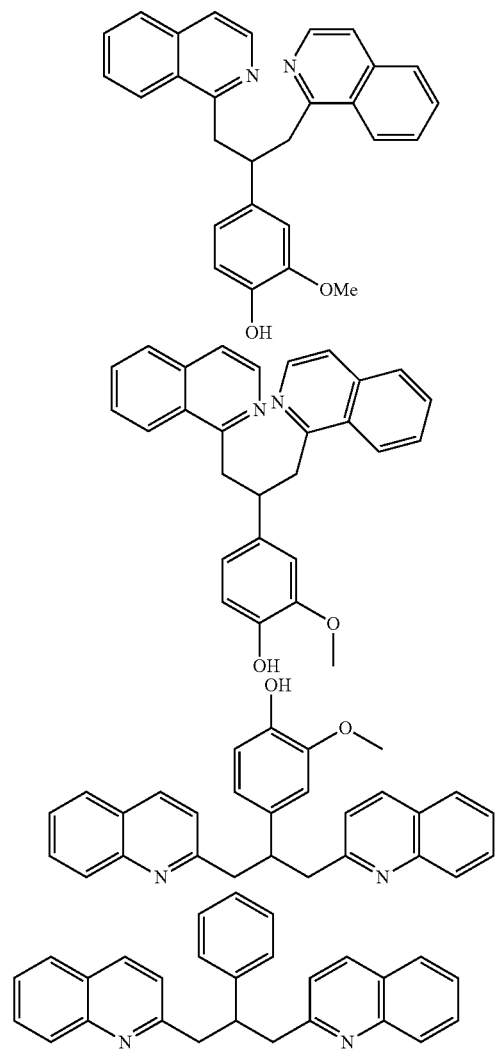

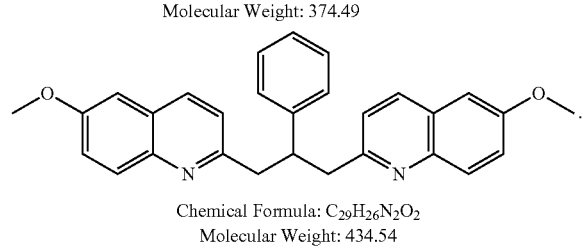

Chemical Formula: $C_{29}H_{26}N_2O_2$
Molecular Weight: 434.54

The tricyclic harmaline/phenyl aldehyde dimers of the invention were prepared via a condensation reaction between two β-carboline molecules (harmaline) and a phenyl aldehyde. Nucleophilic addition of the harmaline enamine to the carbonyl of the aldehyde resulted in the formation of an hydroxyl intermediate, which then underwent additional nucleophilic attack by the enamine-amine of the second harmaline to give the dimeric molecule. While other solvents were explored, methanol was found to provide the best yields for this reaction. This general reaction scheme is set forth below.

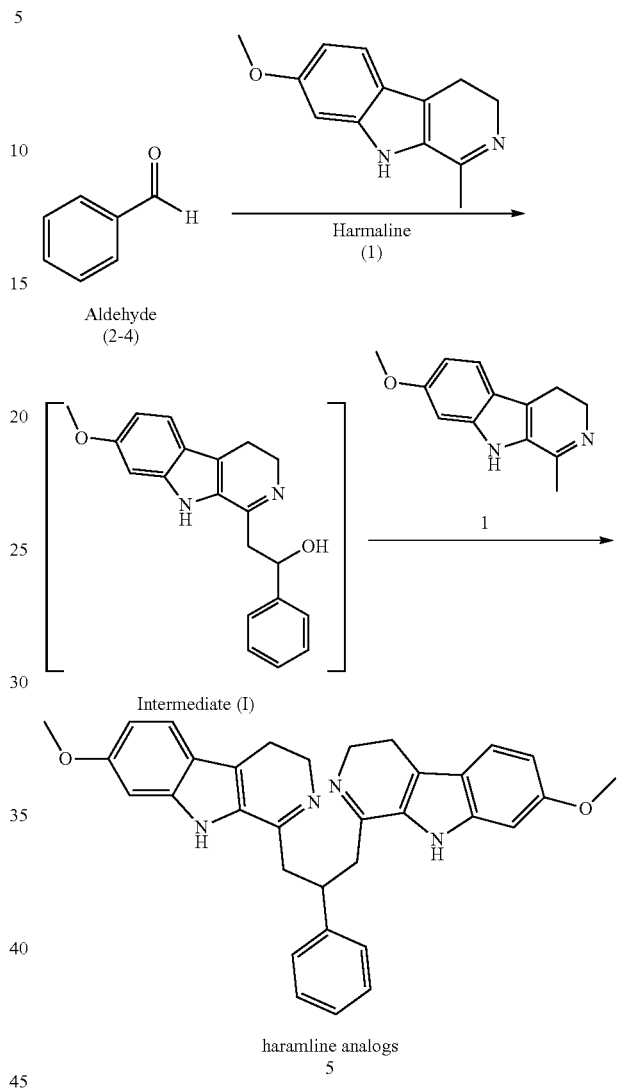

This same procedure was also used to synthesize dimeric analogs of harmaline with vanillin, isovanillin, and benzaldehyde.

Production of the bicyclic/phenyl aldehyde dimers was carried out by refluxing a mixture two equivalents of the appropriate quinoline with one equivalent of the phenyl aldehyde with catalytic p-toluene sulfonic acid (PTSA) in a pressure tube. After completion of the reaction, the solvent was evaporated under reduced pressure, and the residue was purified by column chromatography on silica gel.

Synthesis of the tricyclic compounds with an aliphatic linker involved initially reacting one equivalent of an appropriate diacid with two equivalents of tryptamine overnight at 190° C. Next, the amide was refluxed with POCl3 at 90-100° C. for 3-4 hours, whereupon the solvent was distilled off and the reaction mixture neutralized with 20% sodium hydroxide. In the final step, the aqueous solution was extracted with dichloromethane, dried with sodium sulfate, and purified using column chromatography to yield the aliphatic-linked product.

The following sets forth the general reaction schemes for these three classes of compounds in accordance with the invention. Note that when linkers having 2-4 methylene units were used, the reaction conditions were modified. Specifically, tryptamine was coupled with the corresponding diacid using an amide coupling reaction to give diamide products 20a-20e. These compounds were then subjected to Bischler-Napieralski conditions, which provided the cyclized and dimeric analogs 7-9, containing 3 and 4 methylene units respectively. This cyclization synthesis was not successful using linkers having 0-2 methylene units.

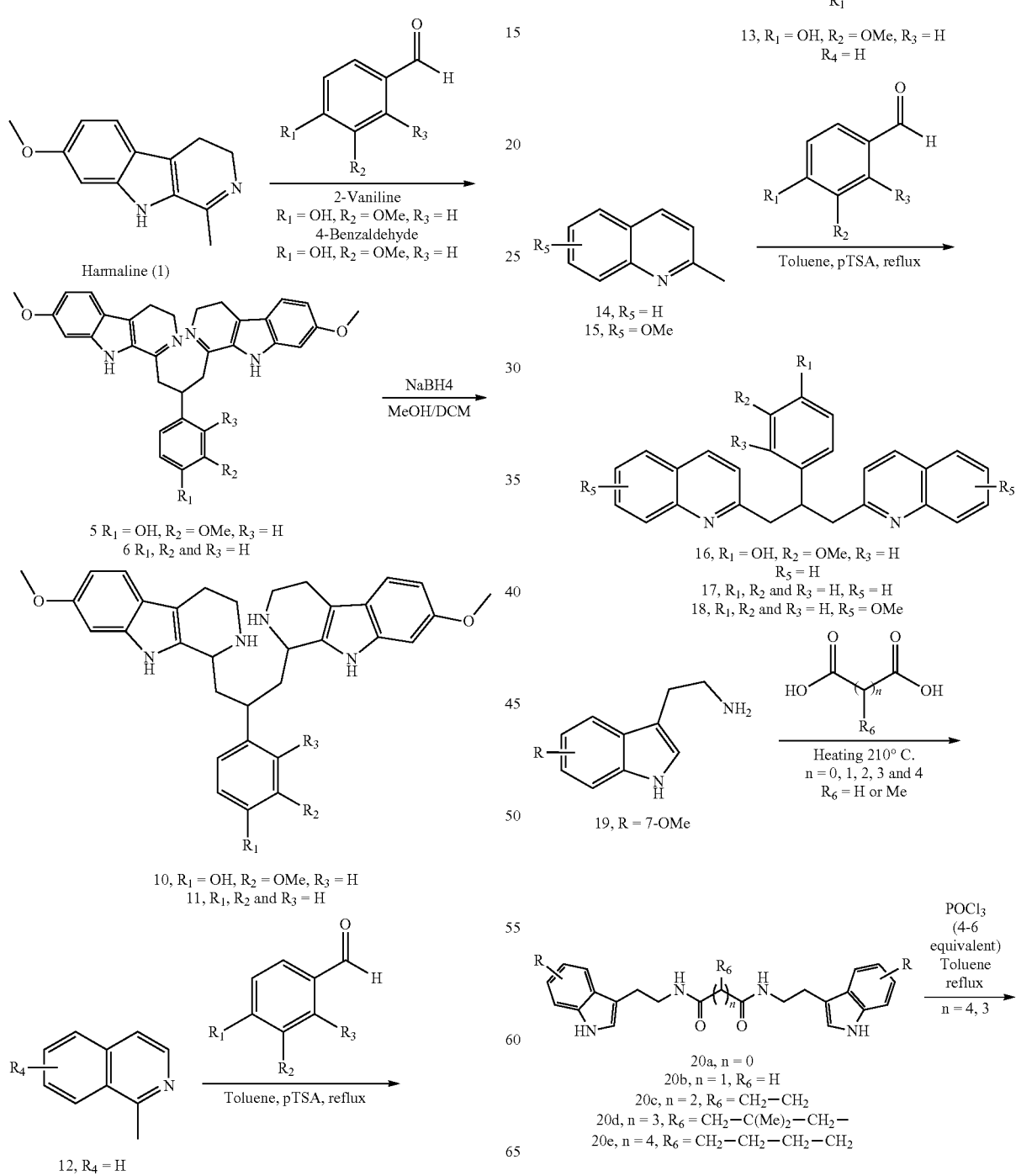

-continued

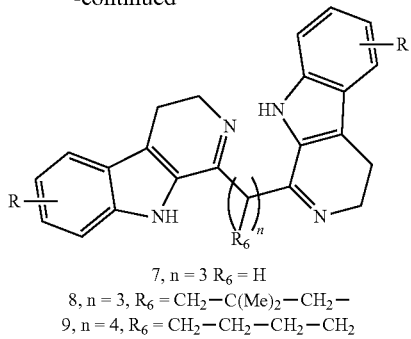

7, n = 3 R$_6$ = H
8, n = 3, R$_6$ = CH$_2$—C(Me)$_2$—CH$_2$—
9, n = 4, R$_6$ = CH$_2$—CH$_2$—CH$_2$—CH$_2$

The invention also provides new methods for treatment of cancers by administration of appropriate quantities of the compounds hereof. Hence, the compositions are particularly designed for use in the treatment of cancers, and the compositions can be used for the manufacture of medicaments for anti-cancer therapeutic applications. In addition, the invention provides compositions for the treatment of cancers comprising administering therapeutically effective amounts of the new compositions, prepared by processes known per se, with a pharmaceutically acceptable carrier.

DETAILED DESCRIPTION OF THE PREFERRED EMBODIMENTS

The therapeutic agents of the invention are used in therapeutically effective amounts, i.e., amounts that will elicit the biological or medical response of a tissue, system, or subject that is being sought, and in particular to elicit some desired therapeutic effect against a variety of human diseases, and especially cancers; in the case of cancers, the agents operate by preventing and/or inhibiting proliferation and/or survival of cancerous cells, including cancer stem cells, and/or by slowing the progression of cancers. Those skilled in the art recognize that an amount may be considered therapeutically effective even if the condition is not totally eradicated or prevented, but it or its symptoms and/or effects are improved or alleviated partially in the subject. Of course, the appropriate makeup of the agents hereof and dosing regimens using such agents will depend on the particular cancer being treated, the extent of the disease, and other factors related to the patient as determined by those skilled in the art. Hence, the terms "therapeutic" or "treat," as used herein, refer to products or processes in accordance with the invention that are intended to produce a beneficial change in an existing condition (e.g., cancerous tissue, tumor size, metastases, etc.) of a subject, such as by reducing the severity of the clinical symptoms and/or effects of the condition, and/or reducing the duration of the symptoms/effects of a subject.

Additional ingredients may be included with the chemotherapeutic agents of the invention for administration to the subject. Such additional ingredients include, other active agents, preservatives, buffering agents, salts, carriers, excipients, diluents, or other pharmaceutically-acceptable ingredients. The active agents that could be included in the compositions include antiviral, antibiotic, or other anticancer compounds; the latter could include the compounds described in PCT application serial number PCT/US2015/055968, such as curcumin, harmine, and isovanillin, and metabolites, dimers, derivatives, isomers, enantiomers (both D and L), tautomers, esters, complexes and salts of any of the foregoing.

The therapeutic agents of the invention give significant and unexpected therapeutic results, particularly in the context of anti-cancer results. In use, a therapeutically effective amount of an agent or composition in accordance with the invention is administered to a subject in need thereof. Such may comprise a single unit dosage or, more usually, periodic (e.g., daily) administration of lower dosages over time.

The dosages may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) administrations. The dosage forms of the invention may be in the form of liquids, gels, suspensions, solutions, or solids (e.g., tablets, pills, or capsules). Moreover, therapeutically effective amounts of the agents of the invention may be co-administered with other chemotherapeutic agent(s), where the two products are administered substantially simultaneously or in any sequential manner.

Levels of dosing using the compositions of the invention are quite variable owing to factors such as the patient's age, patient's physical condition, weight, the type of condition(s) being treated (e.g., specific cancer(s)), and the severity of the conditions. In general, however, regardless of the dosage form or route of administration employed, such as liquid solutions or suspensions, capsules, pills, or tablets, via oral, parenteral, or injection, the compositions should be dosed of from about 5 to 2000 mg per day, and more usually from about 100-800 mg per day. Such dosages may be based on a single administration per day, but more usually multiple administrations per day.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

As used herein, pharmaceutically acceptable salts with reference to the compounds of the present invention mean salts of the compounds which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucametacin acid, gluconic acid, glutamic acid, glycolic acid, heptanoic acid, hexanoic acid, hydroxynaphthoic acid, lactic acid, laurylsulfuric acid, maleic acid, malic acid, malonic acid, Mandela acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties*, and Use, P. H. Stahl & C. G. Wermuth eds., ISBN 978-3-90639-058-1(2008).

As used herein, the terms "alkyl," "alkenyl," "alkynyl," mean and are intended to cover straight, branched chain, and cyclic groups. "Amines" means and is intended to cover primary, secondary, and tertiary amines. "Sulfur groups" means and is intended to cover thiols, sulfides, disulfides, and sulfoxides. "Derivative" means and is intended to cover compounds, moieties, and/or groups which are substituted with atoms, groups, or side chains which do not materially degrade (e.g., no more than about 20%, preferably no more than about 10%, degradation) of the performance of the compound, moiety, or group as compared with the unsubstituted versions thereof.

In the development of the present invention, a series of novel and other compounds were prepared and assayed for anti-cancer activity. Set forth below are the syntheses of the specific compounds, followed by the anti-cancer assay results.

Specific Syntheses of Compounds in Accordance with the Invention

The starting materials, solvents, and reagents were obtained commercially and used directly without purification. The NMR spectra of compounds were recorded on Brüker FT-NMR 400 Hz spectrometer in CDCl$_3$ using tetramethylsilane (TMS) as an internal standard. The δ values represent chemical shifts reported in parts per million (ppm) and coupling constant (J) values are in Hz. $^{13}$C NMR spectra were definitively assigned. ESI-MS and ESI-HRMS were recorded on a Brüker MicroTOF instrument. Flash chromatography was conducted by using Silica size (100-200 mesh). Thin layer chromatography was performed on TLC Silica Gel 60 F254 (Merck).

General Method to Synthesize Compounds 5 and 6

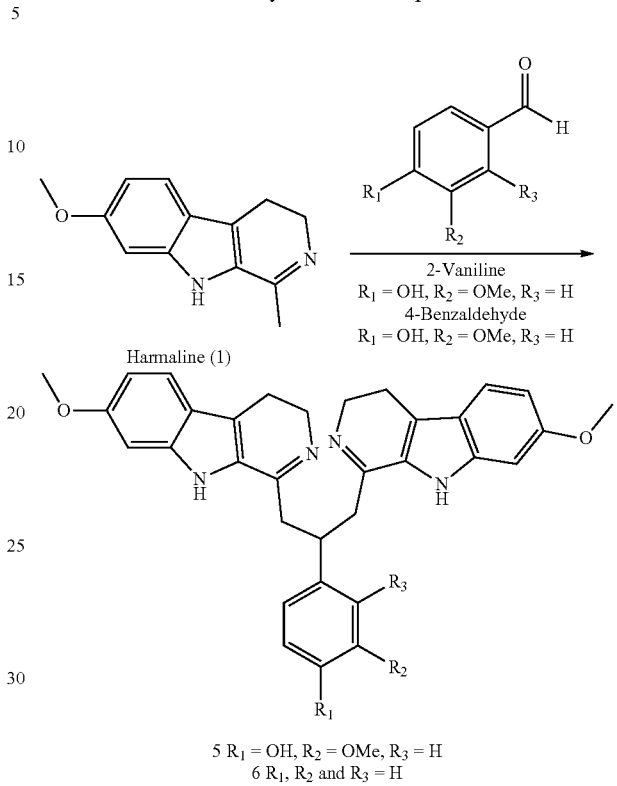

A solution of harmaline (200 mg, 1.31 mmoles, 1 eq) and vanillin (100 mg, 0.655 mmoles, 2 eq) in MeOH (5 ml) was prepared and refluxed for 3-4 hrs. The reaction progress was monitored by TLC with 10% MeOH+90% DCM. (ammonia in DCM or 7N ammonia in MeOH). After completion of the reaction, the reaction mixture was filtered, and crude solid was collected. The resulting crude solid was purified using column chromatography to give compound 5 or 6.

4-(1,3-bis(7-methoxy-4,9-dihydro-3H-pyrido[3,4-b]indol-1-yl)propan-2-yl)-2-methoxy-phenol (Compound 5)

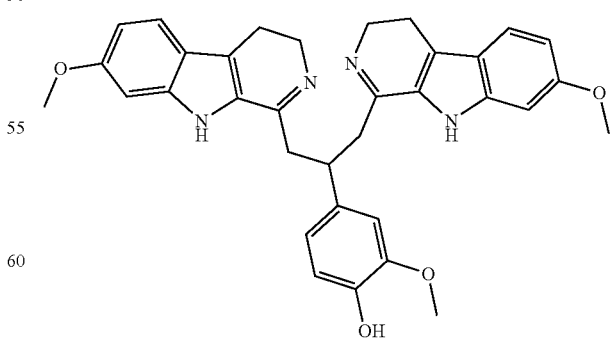

$^1$H NMR (400 MHz, DMSO-d$_6$) δ 10.86 (s, 1H), 10.70 (s, 1H), 8.72 (d, J=12.3 Hz, 1H), 7.27 (t, J=8.6 Hz, 2H), 6.87 (d, J=1.8 Hz, 1H), 6.83-6.69 (m, 4H), 6.69-6.56 (m, 2H), 3.90-3.81 (m, 1H), 3.82 (s, 1H), 3.84-3.71 (m, 8H), 3.70 (d, J=5.7 Hz, 1H), 3.18 (dd, J=11.8, 4.4 Hz, 5H), 3.07 (dd, J=13.2, 6.1 Hz, 1H), 2.95-2.79 (m, 1H), 2.79-2.66 (m, 1H), 2.65 (s, 2H), 2.66-2.52 (m, 1H), 2.28-2.07 (m, 2H). $^{13}$C NMR (101 MHz, CDCl3) δ 164.99, 162.53, 146.89, 145.13, 144.90, 130.60, 126.55, 125.61, 122.38, 120.95, 119.12, 116.33, 114.08, 109.49, 93.66, 77.35, 77.03, 76.72, 55.79, 55.64, 41.99, 37.40, 19.92. HRMS (ESI+), m/z [M+H$^+$] calculated for $C_{34}H_{35}N_4O_4$ 563.2674; found 563.2674.

1,1'-(2-phenylpropane-1,3-diyl)bis(7-methoxy-4,9-dihydro-3H-pyrido[3,4-b]indole) (Compound 6)

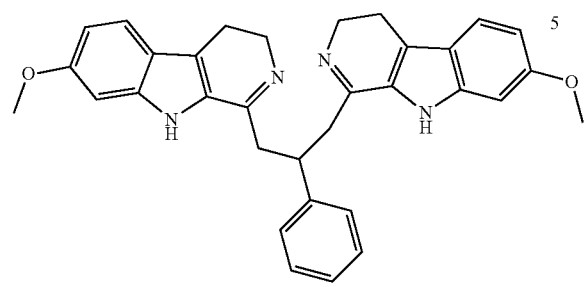

1H NMR (400 MHz, Chloroform-d) δ 12.24 (s, 1H), 11.97 (s, 1H), 7.32 (dd, J=15.2, 8.3 Hz, 4H), 7.06 (dt, J=28.8, 7.4 Hz, 4H), 6.93 (d, J=2.2 Hz, 2H), 6.74 (dd, J=9.0, 2.1 Hz, 2H), 4.58 (t, J=8.5 Hz, 1H), 3.85 (s, 6H), 3.58 (dt, J=21.8, 14.1 Hz, 8H), 2.93-2.84 (m, 4H). $^{13}$C NMR (101 MHz, CDCl$_3$) δ 156.22, 145.78, 144.78, 136.65, 129.05, 128.98, 128.66, 127.86, 127.54, 126.89, 126.76, 121.67, 119.17, 118.75, 118.55, 118.48, 108.60, 95.11, 55.84, 55.77, 50.64, 40.85, 40.36, 31.95, 29.73, 22.72, 14.15. HRMS (ESI+), m/z [M+H$^+$] calculated for $C_{33}H_{33}N_4O_4$ 517.6578; found 517.2253.

General Method to Synthesize Analogs 10 and 11

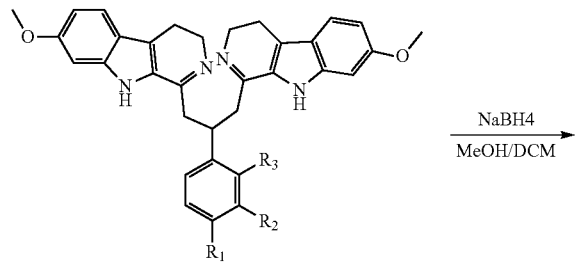

5 $R_1$ = OH, $R_2$ = OMe, $R_3$ = H
6 $R_1$, $R_2$ and $R_3$ = H

NaBH4 / MeOH/DCM

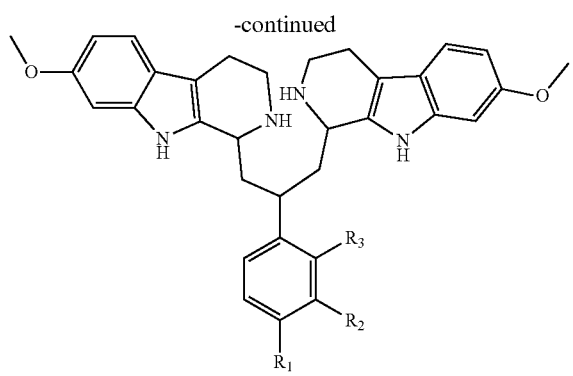

10, $R_1$ = OH, $R_2$ = OMe, $R_3$ = H
11, $R_1$, $R_2$ and $R_3$ = H

A solution of 5 or 6 (30 mg, 0.0533 mmoles, 1 equivalent) in dichloromethane (DCM, 1.5 ml) was prepared, and methanol (5 ml) and sodium borohydride (10 mg, 0.266 mmoles, 5 equivalent) were added slowly at 0° C. temperature. (Before addition of sodium borohydride, the reaction mixture was unclear or partially soluble). The reaction mixture was stirred at room temperature for overnight period. The reaction progress was monitored by TLC with 10% MeOH+90% DCM. (ammonia in DCM or 7N ammonia in MeOH). After completion of the reaction, reaction mixture was quenched by addition of 20 ml of water and extracted with DCM (20 ml×2 times). The organic layer was wash with brine, dried over sodium sulphate. The crude oily brown material was purified with column chromatography to give 10 and 11.

4-(1,3-bis(7-methoxy-2,3,4,9-tetrahydro-1H-pyrido[3,4-b]indol-1-yl)propan-2-yl)-2-methoxyphenol (Analog 10)

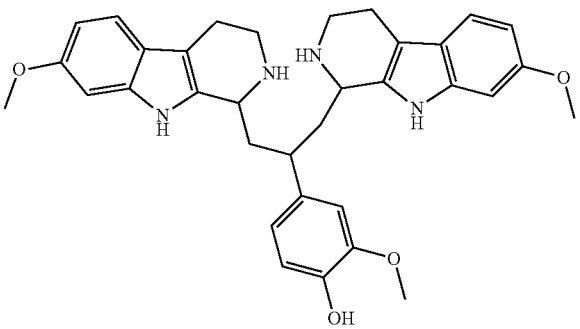

Chemical Formula: $C_{34}H_{38}N_4O_4$
Molecular Weight: 566.70

$^1$H NMR (400 MHz, DMSO-d$_6$) δ 10.86 (s, 1H), 10.70 (s, 1H), 8.72 (d, J=12.3 Hz, 1H), 7.27 (t, J=8.6 Hz, 2H), 6.87 (d, J=1.8 Hz, 1H), 6.83-6.69 (m, 4H), 6.69-6.56 (m, 2H), 3.90-3.81 (m, 1H), 3.82 (s, 1H), 3.84-3.71 (m, 8H), 3.70 (d, J=5.7 Hz, 1H), 3.18 (dd, J=11.8, 4.4 Hz, 5H), 3.07 (dd, J=13.2, 6.1 Hz, 1H), 2.95-2.79 (m, 1H), 2.79-2.66 (m, 1H), 2.65 (s, 2H), 2.66-2.52 (m, 1H), 2.28-2.07 (m, 2H). $^{13}$C NMR (101 MHz, Chloroform-d) δ 155.08, 146.22, 143.76, 135.63, 133.48, 120.74, 118.57, 117.47, 117.37, 114.17, 109.65, 107.70, 107.45, 94.40, 94.15, 54.79, 54.38, 50.23, 40.68, 40.15, 39.07, 28.68, 21.67, 18.13. HRMS (ESI+), m/z [M+H$^+$] calculated for $C_{34}H_{38}N_4O_4$ 567.7058; found 567.6998.

1,1'-(2-phenylpropane-1,3-diyl)bis(7-methoxy-2,3,4,9-tetrahydro-1H-pyrido[3,4-b]indole) (Analog 11)

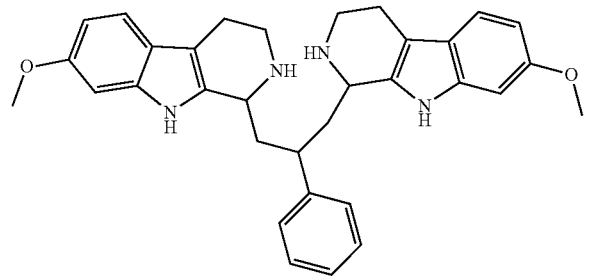

Chemical Formula: $C_{33}H_{36}N_4O_2$
Molecular Weight: 520.68

1H NMR (400 MHz, Chloroform-d) δ 12.21 (s, 2H), 11.97 (s, 2H), 7.33 (dd, J=16.8, 8.3 Hz, 4H), 7.10 (t, J=7.4 Hz, 2H), 7.03 (t, J=7.3 Hz, 1H), 6.93 (d, J=2.2 Hz, 2H), 6.74 (dd, J=9.0, 2.2 Hz, 2H), 4.59 (t, J=8.6 Hz, 1H), 3.85 (s, 6H), 3.58 (dt, J=21.8, 13.4 Hz, 3H), 2.89 (dd, J=10.1, 7.3 Hz, 4H). $^{13}$C NMR (101 MHz, CDCl3) δ 156.22, 145.78, 144.78, 136.65, 129.05, 128.98, 128.66, 127.86, 127.54, 126.89, 126.76, 121.67, 119.17, 118.75, 118.55, 118.48, 108.60, 95.11, 55.84, 55.77, 50.64, 40.85, 40.36, 31.95, 29.73, 22.72, 14.15. HRMS (ESI+), m/z [M+H$^+$] calculated for $C_{33}H_{37}N_4O_4$ 521.6578; found 521.2253.

General Method to Synthesize Compounds 13 and 16-18

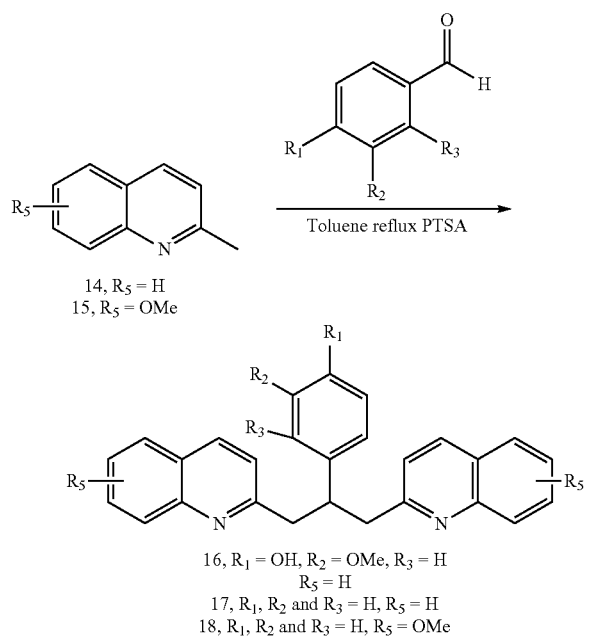

16, $R_1$ = OH, $R_2$ = OMe, $R_3$ = H
$R_5$ = H
17, $R_1$, $R_2$ and $R_3$ = H, $R_5$ = H
18, $R_1$, $R_2$ and $R_3$ = H, $R_5$ = OMe p-Toluenesulfonic acid (PTSOH 0.2 eq, 26 μmol), 6-methoxy-2-methylquinoline (2 eq, 1.1 mmol) and vanillin (1 eq, 0.53 mmol) were mixed in a pressure tube and then dry Toluene (3 mL) was added. The mixture was stirred at 120° C. in closed pressure tube. The reaction was monitored by TLC. After completion of the reaction, the solvent was evaporated under reduced pressure and the residue was purified by column chromatography on silica gel.

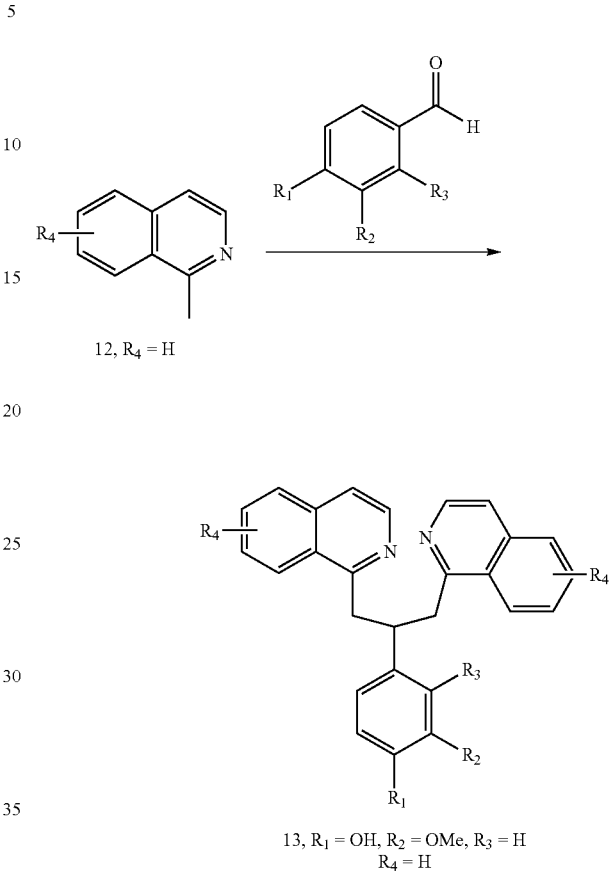

13, $R_1$ = OH, $R_2$ = OMe, $R_3$ = H
$R_4$ = H 4-(1,3-di(isoquinolin-1-yl)propan-2-yl)-2-methoxyphenol (Compound 13)

$^1$H NMR (400 MHz, Chloroform-d) δ 8.27 (d, J=5.7 Hz, 2H), 8.02 (d, J=8.5 Hz, 2H), 7.74-7.67 (m, 2H), 7.66-7.54 (m, 1H), 7.59-7.41 (m, 3H), 7.40 (dd, J=15.5, 5.6 Hz, 3H), 7.20 (s, 1H), 6.68 (dd, J=8.1, 2.0 Hz, 1H), 6.51 (d, J=8.1 Hz, 1H), 6.46 (d, J=2.0 Hz, 1H), 4.04 (p, J=7.4 Hz, 1H), 3.74 (dd, J=13.9, 7.3 Hz, 2H), 3.60 (dd, J=13.9, 7.4 Hz, 2H), 3.54 (s, 3H). HRMS (ESI+), m/z [M+H$^+$] calculated for $C_{28}H_{25}N_4O_4H$, 421.5136; found 421.5106.

4-(1,3-di(quinolin-2-yl)propan-2-yl)-2-methoxyphenol (Compound 16)

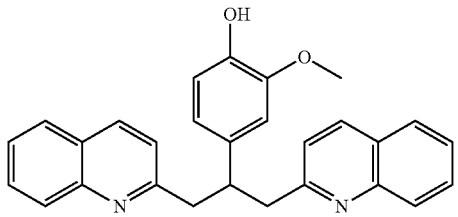 [SMILES: COc1cc(C(Cc2ccc3ccccc3n2)Cc2ccc3ccccc3n2)ccc1O]

$^1$H NMR (400 MHz, Chloroform-d) δ 7.94 (dd, J=8.5, 1.1 Hz, 2H), 7.81 (dd, J=8.5, 0.8 Hz, 2H), 7.65-7.53 (m, 4H), 7.37 (ddd, J=8.1, 6.9, 1.2 Hz, 2H), 7.03 (d, J=8.4 Hz, 2H), 6.66-6.57 (m, 2H), 6.55 (d, J=1.7 Hz, 1H), 5.66 (s, 1H), 3.87 (tt, J=8.4, 6.8 Hz, 1H), 3.55 (d, J=2.3 Hz, 1H), 3.54 (s, 2H), 3.36 (dd, J=13.6, 6.8 Hz, 2H), 3.29 (dd, J=13.6, 8.5 Hz, 2H). $^{13}$C NMR (101 MHz, Chloroform-d) δ 160.87, 146.26, 143.94, 135.94, 135.40, 129.32, 128.64, 127.47, 126.69, 125.79, 122.17, 120.33, 114.21, 110.76, 55.73, 45.84, 45.80. HRMS (ESI+), m/z [M+H$^+$] calculated for $C_{28}H_{25}N_2O_2$ 421.1933; found 421.1910.

2,2'-(2-phenylpropane-1,3-diyl)diquinoline (Compound 17)

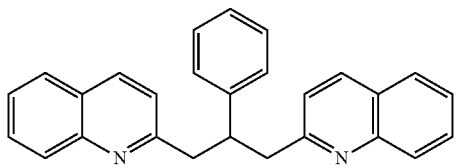

Chemical Formula: $C_{27}H_{22}N_2$
Molecular Weight: 374.49

$^1$H NMR (400 MHz, Chloroform-d) δ 8.09-8.02 (m, 1H), 7.86 (dd, J=8.4, 0.8 Hz, 1H), 7.66 (td, J=8.3, 1.2 Hz, 2H), 7.44 (td, J=7.3, 1.2 Hz, 1H), 7.28-7.21 (m, 1H), 7.25-7.14 (m, 1H), 7.18-7.06 (m, 2H), 4.07 (tt, J=8.4, 6.8 Hz, 1H), 3.56-3.37 (m, 2H). $^{13}$C NMR (101 MHz, Chloroform-d) δ 160.76, 147.83, 143.77, 135.76, 129.21, 128.85, 128.28, 127.94, 127.46, 126.69, 126.32, 125.71, 122.11, 46.17, 45.76. HRMS (ESI+), m/z [M+Na$^+$] calculated for $C_{27}H_{23}N_2Na$, 375.1888; found 375.1855.

2,2'-(2-phenylpropane-1,3-diyl)bis(6-methoxyquinoline) (Compound 18)

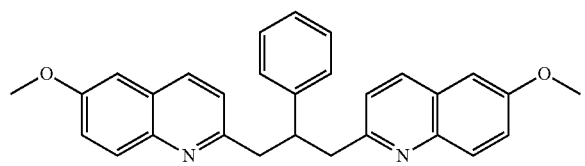

Chemical Formula: $C_{29}H_{26}N_2O_2$
Molecular Weight: 434.54

$^1$H NMR (400 MHz, Chloroform-d) δ 7.92 (d, J=9.2 Hz, 1H), 7.72 (dd, J=8.5, 0.7 Hz, 1H), 7.30 (dd, J=9.2, 2.8 Hz, 1H), 7.25-7.16 (m, 1H), 7.19-7.06 (m, 1H), 7.10-6.99 (m, 1H), 6.89 (d, J=2.8 Hz, 1H), 4.05-3.93 (m, OH), 3.83 (s, 3H), 3.44 (dd, J=13.7, 6.9 Hz, 1H), 3.36 (dd, J=13.7, 8.3 Hz, 1H). $^{13}$C NMR (101 MHz, CDCl$_3$) δ 158.19, 157.12, 143.98, 143.82, 134.60, 130.19, 128.22, 127.93, 127.50, 126.21, 122.35, 121.72, 105.05, 77.39, 77.08, 76.76, 55.47, 46.32, 45.48. HRMS (ESI+), m/z [M+Na$^+$] calculated for $C_{29}H_{26}N_2O_2Na$, 457.1914; found 457.1886.

Methods to Synthesize Analogs 7, 8, 9

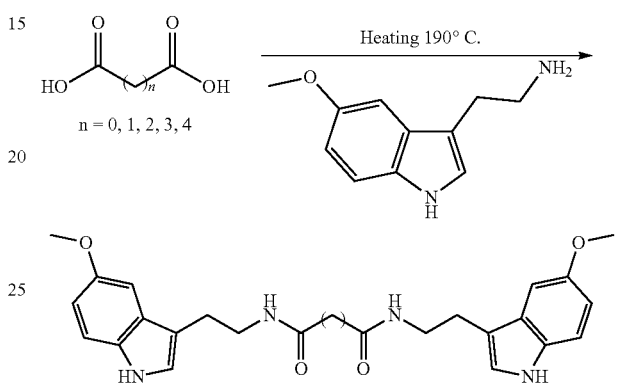

A di-acid (1.4 mmoles, 1 equivalent) and 2-(5-methoxy-1H-indol-3-yl)ethan-1-amine (2.4 mmoles, 2 equivalent) were mixed together and heated at 190° C. for overnight period. After completion of the reaction, the product was diluted with methanol and dichloromethane (4:4 ml), purified with column chromatography to give an amide.

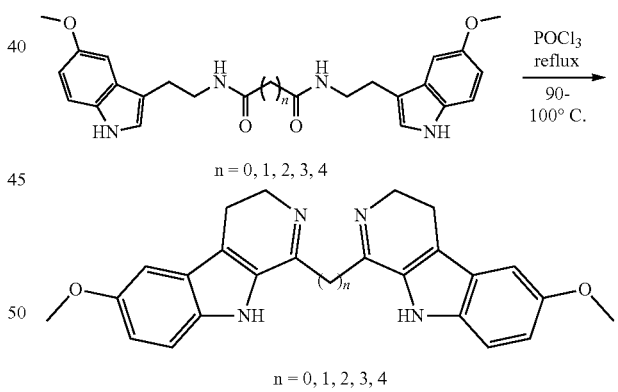

A solution of N1,N5-bis(2-(5-methoxy-1H-indol-3-yl)ethyl)glutaramide (1 eq, 0.4 mmol) in Toluene (2 mL) was prepared, and dichloromethane (2 mL) and phosphorous oxychloride (POCl3 1.5 mmole, 0.14 mL) was added. The reaction mixture was heated at reflux temperature for 3-4 hrs. After completion of the reaction, the solvent was distilled off and the reaction mixture was neutralized with 20% NaOH (10 ml). The aqueous solution was then extracted with dichloromethane (2×20 ml dichloromethane), dried with sodium sulfate and then purified with column chromatography to give 1,3-bis(6-methoxy-4,9-dihydro-3H-pyrido[3,4-b]indol-1-yl)propane.

1,3-bis(6-methoxy-4,9-dihydro-3H-pyrido[3,4-b]indol-1-yl)propane (Analog 7)

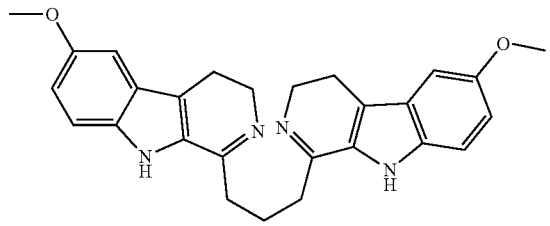

$^1$H NMR (400 MHz, Chloroform-d) δ 13.12 (s, 1H), 12.29 (s, 1H), 7.43 (d, J=9.2 Hz, 1H), 7.07 (dd, J=9.2, 2.4 Hz, 1H), 6.77 (d, J=2.4 Hz, 1H), 3.86 (td, J=8.7, 3.1 Hz, 2H), 3.78 (s, 3H), 3.29-3.20 (m, 2H), 3.11 (t, J=8.7 Hz, 2H), 2.50 (td, J=16.9, 14.6, 7.5 Hz, 1H). $^{13}$C NMR (101 MHz, MeOD) δ 155.68, 124.81, 113.86, 54.62, 46.95, 42.44, 23.90, 18.71. HRMS (ESI+), m/z [M+H$^+$] calculated for $C_{27}H_{29}N_4O_2$ 441.2279; found 441.2285.

1,1'-(2,2-dimethylpropane-1,3-diyl)bis(6-methoxy-4,9-dihydro-3H-pyrido[3,4-b]indole) (Analog 8)

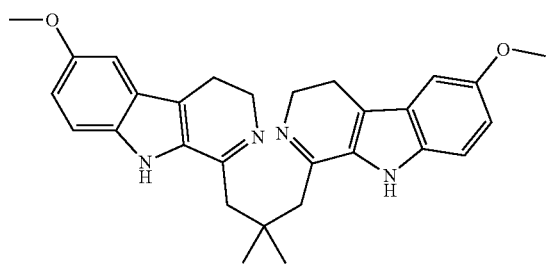

$^1$H NMR (400 MHz, Chloroform-d) δ 11.36 (s, 1H), 7.33 (dd, J=8.8, 1.4 Hz, 2H), 7.01 (d, J=2.3 Hz, 2H), 6.96 (dt, J=8.8, 2.1 Hz, 2H), 4.01 (q, J=8.7, 7.5 Hz, 4H), 3.89 (d, J=1.6 Hz, 6H), 2.92 (td, J=8.3, 1.7 Hz, 4H), 2.69 (d, J=8.0 Hz, 2H), 1.05 (d, J=5.0 Hz, 6H). $^{13}$C NMR (101 MHz, Chloroform-d) δ 160.95, 154.36, 132.23, 130.67, 125.63, 116.19, 115.67, 113.21, 100.42, 55.82, 47.79, 43.71, 35.87, 30.00, 19.47. HRMS (ESI+), m/z [M+H$^+$] calculated for $C_{29}H_{33}N_4O_4$ 469.2610; found 469.2598.

1,4-bis(6-methoxy-4,9-dihydro-3H-pyrido[3,4-b]indol-1-yl)butane (Analog 9)

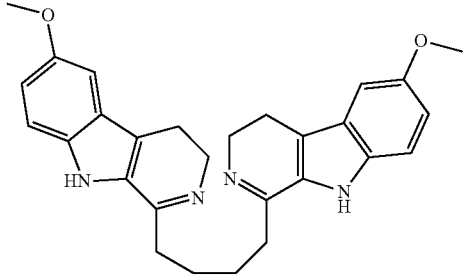

Chemical Formula: $C_{28}H_{30}N_4O_2$
Molecular Weight: 454.57

$^1$H NMR (400 MHz, Chloroform-d) δ 7.50 (d, J=9.2 Hz, 2H), 7.06 (dd, J=9.2, 2.4 Hz, 2H), 6.78 (d, J=2.4 Hz, 2H), 3.89 (t, J=8.5 Hz, 4H), 3.78 (s, 6H), 3.21 (s, 1H), 3.11 (t, J=8.7 Hz, 4H), 2.08 (s, 4H), 1.18 (s, 3H). $^{13}$C NMR (101 MHz, Chloroform-d) δ 122.89, 115.48, 99.28, 55.59, 50.15, 49.94, 49.72, 42.28, 19.63. HRMS (ESI+), m/z [M+H$^+$] calculated for $C_{28}H_{30}N_4O_4$ 455.5789; found 455.5678.

The following Table sets forth the IC$_{50}$ values of harmaline and quinoline analogs against 23 human cancer cell lines. Growth inhibition effects (in vitro cytotoxicity) on pancreatic, endometrial, breast, lung, ovarian, renal, cervical, lymphoma, and myeloma cancer cells were determined by MTT assays and represented by average IC$_{50}$ values. In the Table, the results are given in terms of μM, and nd=not determined.

| | Cell line | | | | | | | | | | |
|---|---|---|---|---|---|---|---|---|---|---|---|
| | 5 | 6 | 7 | 8 | 9 | 10 | 11 | 13 | 16 | 17 | 18 |
| MIA Paca-2 | 2.87 | 1.85 | 4.54 | 1.22 | 6.58 | 2.53 | 2.25 | 19.71 | 24.49 | 13.33 | 21.88 |
| ASPC-1 | 6.75 | 2.08 | 7.9 | 2.07 | 20.25 | 4.62 | 2.4 | 49.03 | 94.57 | 28.67 | >100 |
| BxPC-3 | 2.11 | nd | 3.21 | 0.95 | 10.66 | nd | nd | 20.05 | 19.52 | 7.64 | 25.13 |
| AN3CA | 2.5 | nd | 3.01 | 1.96 | 20.66 | nd | nd | 19.5 | 19.68 | 9.35 | 41.83 |
| HEC-1a | 5.05 | nd | 7.02 | 2.22 | 20.67 | nd | nd | 39.82 | 67.68 | 25.43 | 37.65 |
| MDA-MB-231 | 2.52 | nd | 3.12 | 1.5 | 19.39 | nd | nd | 28.19 | 31.62 | 14.46 | >100 |
| MDA-MB-468 | 2.76 | nd | 2.6 | 1.9 | 7.09 | nd | nd | 19.58 | 31.63 | 25.81 | >100 |
| HCC70 | 2.38 | nd | 5.13 | 1.3 | 11.87 | nd | nd | 37.17 | 35.18 | 17.18 | >100 |
| H1975 (EGFR mut) | 6.12 | nd | 5.77 | 2.08 | 19.06 | nd | nd | 42.2 | 58.9 | 30.09 | >100 |
| H1650(EGFR mut) | 2.78 | nd | 4.95 | 1.78 | 15.1 | nd | nd | 38.14 | 50.99 | 24.63 | 48.5 |
| A2780 | 5 | 2.95 | 2.54 | 1.38 | 11.62 | 6.14 | 3.4 | 27.23 | 29.7 | 13.34 | 25.57 |
| A2780CP | 3.76 | nd | 4.12 | 2.23 | 17.79 | nd | nd | 25.13 | 22.26 | 9 | 26.61 |
| A498 | 3.56 | nd | 5.39 | 1.71 | 19.15 | nd | nd | 38.53 | 81.31 | 21.93 | >100 |
| SiHA | 4.88 | nd | 12.65 | 2.89 | 19.74 | nd | nd | 45.21 | 84.28 | 23.47 | >100 |
| FaDu | 3.87 | 1.58 | 2.34 | 0.98 | 6.82 | 2.61 | 2.22 | 33.61 | 49.19 | 18.64 | 30.33 |
| DoHH-2 | 1.83 | 1.98 | 2.41 | 2.21 | 6.48 | 2.24 | 2.31 | 19.52 | 14.84 | 6.9 | 14.29 |
| OCI-LY3 | 4.54 | nd | 8.85 | 2.59 | 6.99 | nd | nd | 36.73 | 77.5 | 23.79 | 42.24 |
| JIM1 | 3.17 | 2.22 | 6.15 | 2.59 | 21.14 | 2.27 | 2.42 | 29.18 | 35.36 | 10.99 | 31.73 |
| KMM-1 | 3.48 | 1.91 | 5.18 | 1.49 | 12.16 | 2.53 | 2.05 | 14.81 | 17 | 7.99 | 14.81 |
| KMS-34 | 4.72 | nd | 4.41 | 1.7 | 15.14 | nd | nd | 11.76 | 14.81 | 7.85 | 17.19 |
| RPMI-8226 | 3.19 | nd | 1.97 | 0.81 | 5.54 | nd | nd | 17.99 | 15.24 | 7.92 | 17.83 |
| L363 | 2.69 | 1.4 | 2.47 | 1.21 | 8.34 | 2.17 | 1.92 | 29.18 | 29.54 | 7.99 | 17.38 |
| MOLP-8 | 3.37 | nd | 1.88 | 0.67 | 3.68 | nd | nd | 9.71 | 16.03 | 6.56 | 14.97 |

As is evident from the foregoing, compounds 5-11 and 13-18 demonstrated growth inhibition against human cancer cell lines. For example, compounds 5 and 6 displayed cancer cell growth inhibition at 4-7 μM, which are more potent than harmaline and vanillin (25 and 40 μM for harmaline and vanillin, respectively). The data also revealed that the hydroxy and methoxy groups present in compounds 5 and 10 are not required for anti-cancer activity, which was confirmed with compounds 6 and 11, which lack these substituents but exhibit cancer cell growth inhibition at similar concentrations ($IC_{50}$, 2-4 μM). In addition, reduction of the imine on compounds 5 and 6 into the corresponding secondary amines did not significantly affect the $IC_{50}$ values. The data derived from the four quinoline-based and isoquinoline-based dimeric compounds 13 and 16-18 demonstrated that these compounds less efficacious as compared to compounds 5-6 and 10-11, indicating that the tricyclic rido[3,4-b]indole ring system is preferred for better anti-cancer activity. Compounds 7 and 8 were found to be the most potent compounds, giving $IC_{50}$ values of from 0.6-2 μM.

Compounds 5, 7, and 8 had metabolic half-lives of 76.8±2.36 minutes, 155.90±7.43 minutes, and 412.50±116.67 minutes, respectively.

As is evident from a consideration of the dimers of the invention, in preferred forms, the linker is bonded to terminal cyclic groups of the two fused tricyclic moieties; moreover, in many cases, such linker bonding occurs at methyl substituents of the terminal cyclic groups, such as in the case of harmaline

We claim:

1. A compound having the structure

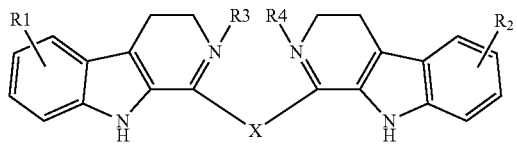

and the derivatives, isomers, enantiomers, tautomers, esters, complexes, and salts thereof, where R1 and R2 are independently selected from the group consisting of H, C1-C4 alkyl groups, and C1-C4 alkoxy groups, R3 and R4 are independently selected from the group consisting of nothing, H, and C1-C2 alkyl groups, and X is selected from the group consisting of (CH2)3 and C3-C8 geminal alkyl groups having a carbon atom therein with two functional groups bound to said carbon atom, said functional groups independently selected from the group consisting of C1-C3 alkyl groups, C1-C3 alcohols, and metal atoms.

2. The compound of claim 1, where R1 and R2 are each methoxy groups.

3. The compound of claim 1, where R3 and R4 are both nothing.

4. The compound of claim 1, where X is a (CH2)3 group.

5. The compound of claim 1, where X is a C3 geminal alkyl group, with said functional groups bound to said carbon atom both being methyl groups.

6. The compound of claim 1, said compound having the structure

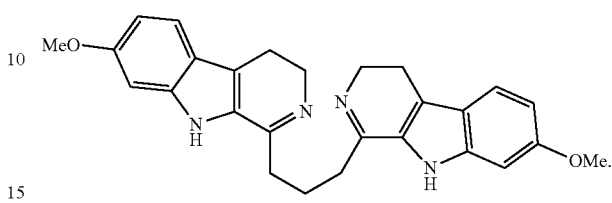

7. The compound of claim 1, said compound having the structure

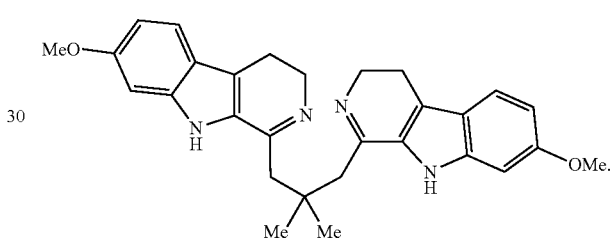

8. The compound of claim 1, said compound being an anti-cancer agent effective against pancreatic, endometrial, breast, lung, ovarian, renal, cervical, lymphoma, and myeloma cancer cells.

9. A therapeutic composition comprising a compound in accordance with claim 1, in combination with one or more of other active agents, preservatives, buffering agents, salts, carriers, excipients, diluents, or other pharmaceutically-acceptable ingredients.

10. A method of treating a human subject suffering from cancer, comprising the step of administering to the subject a compound in accordance with claim 1.

11. A compound having the structure

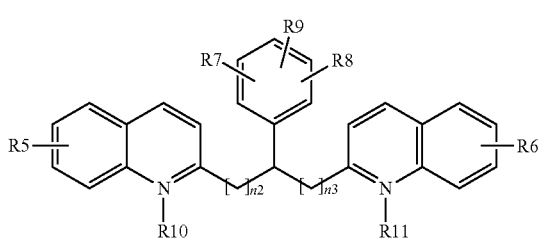

-continued

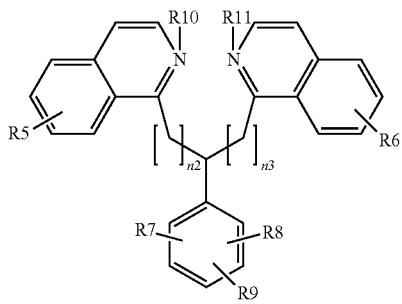

and and the derivatives, isomers, enantiomers, tautomers, esters, complexes, and salts thereof, where R5 and R6 are independently selected from the group consisting of H, C1-C4 alkyl groups, and C1-C4 alkoxy groups, R7, R8, and R9 are independently selected from the group consisting of H, OH, C1-C4 alkoxy groups, C1-C4 alkyl groups, —N2, and CH2N2, and n2 and n3 are independently 1-4, and R10 and R11 are independently selected from the group consisting of nothing, H, and C1-C2 alkyl groups, and wherein at least one of said R7, R8, or R9 substituents is selected from the group consisting of N2 and CH2N2.

12. A therapeutic composition comprising a compound in accordance with claim 11, in combination with one or more of other active agents, preservatives, buffering agents, salts, carriers, excipients, diluents, or other pharmaceutically-acceptable ingredients.

13. A compound of the structure

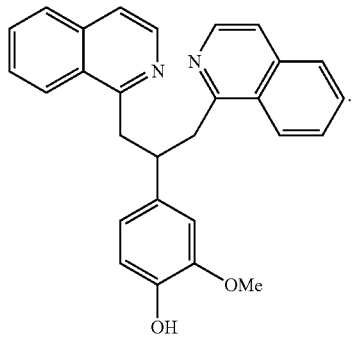 [SMILES: COc1cc(C(Cc2nccc3ccccc23)Cc2nccc3ccccc23)ccc1O]

14. A method of treating a human subject suffering from cancer, comprising the step of administering to the subject a compound in accordance with claim 11.

15. A method of treating a human subject suffering from cancer, comprising the step of administering to the subject a compound in accordance with claim 13.

* * * * *